United States Patent
Kelling

(10) Patent No.: US 7,118,540 B2
(45) Date of Patent: Oct. 10, 2006

(54) METHOD FOR USE IN ORTHODONTICS FOR ACCELERATING TOOTH MOVEMENT WHEN TREATING PATIENTS FOR MALOCCLUSION

(76) Inventor: Albert L. Kelling, 5200 Richland Dr., Raleigh, NC (US) 27612

( * ) Notice: Subject to any disclaimer, the term of this patent is extended or adjusted under 35 U.S.C. 154(b) by 217 days.

(21) Appl. No.: 10/384,340

(22) Filed: Mar. 7, 2003

(65) Prior Publication Data
US 2004/0049133 A1    Mar. 11, 2004

Related U.S. Application Data

(60) Provisional application No. 60/408,911, filed on Sep. 6, 2002.

(51) Int. Cl.
*A61H 1/00*    (2006.01)
(52) U.S. Cl. ............... 601/2; 601/1; 601/3; 601/4; 600/437; 600/439
(58) Field of Classification Search ............ 601/2; 604/22; 443/2, 5, 6, 25, 118, 119, 215, 229
See application file for complete search history.

(56) References Cited

U.S. PATENT DOCUMENTS 4,348,178 A * 9/1982 Kurz .................. 433/6
5,496,256 A * 3/1996 Bock et al. .............. 601/2
6,719,449 B1 * 4/2004 Laugharn et al. ......... 366/127

* cited by examiner

*Primary Examiner*—Brian L. Casler
*Assistant Examiner*—William Jung
(74) *Attorney, Agent, or Firm*—Gardner Groff Santos & Greenwald, PC

(57) ABSTRACT

A method for accelerating orthodontic treatment of malocclusion by noninvasively altering a condition of bone in a patient's jaw so that teeth held in generally fixed positions in the bone are able to be relatively easily and rapidly repositioned using orthodontic appliances. The alteration may be fracturing the medullary and/or cortical bone around the teeth and/or altering vascular, nerve and/or cellular characterisitics of the medullar and/or cortical bone. Once this has been accomplished, typical appliances are used for treatment of malocclusion. Because the medullary and/or cortical bone has been fractured, and/or vascular, nerve and/or cellular characterisitics of the medullary and/or cortical bone have been altered, the appliances used to move the teeth to correct for malocclusion are capable of moving the teeth more rapidly, thereby enabling the process of treating malocclusion to be significantly accelerated in comparison to typical processes used for treatment of malocclusion. In accordance with one embodiment, shock waves are used to alter the condition of bone in the patient's jaw. In accordance with another embodiment, tuned and sustained ultrasound waves and/or high intensity focused ultrasound (HIFU) waves are used to alter the condition of bone in the patient's jaw.

10 Claims, 4 Drawing Sheets

METHOD FOR USE IN ORTHODONTICS FOR ACCELERATING TOOTH MOVEMENT WHEN TREATING PATIENTS FOR MALOCCLUSION

CROSS-REFERENCE TO RELATED APPLICATIONS

This application claims priority to provisional application Ser. No. 60/408,911, filed on Sep. 6, 2002, entitled "A NON-INVASIVE METHOD FOR ACCELERATING ORTHODONTIC TOOTH MOVEMENT", which is incorporated herein by reference in its entirety.

TECHNICAL FIELD OF THE INVENTION

The present invention relates to methods of orthodontic treatment and, more particularly, to methods for accelerating orthodontic tooth movement by utilizing one or more non-invasive procedures.

BACKGROUND OF THE INVENTION

The use of shock waves in the medical community is not new. Early approaches of using shock waves for medical treatment required immersing the patient in water and directing a shock wave, generated by an underwater spark discharge, at a solid site to be treated, such as a bone or kidney stone. When the shock wave hits the solid site, a liberation of energy from the change of acoustic impedance from water to the solid site produces pressure in the immediate vicinity of the site. For example, U.S. Pat. No. 4,905,671 to Senge et al., issued on Mar. 6, 1990, teaches a method applying acoustic shock waves to induce bone formation. Senge et al. utilizes the extremely short rise time of the shock wave to create high compression zones within bone tissue to cause reactions of the microcompartments of the bone. Senge et al. purports that such reactions cause the formation of hematomas within bone, which in turn, induce the formation of new bone.

Senge et al. utilizes a shock wave source consisting of a spark gap between electrodes within a container of water. An electrical condenser connected to the electrodes releases its energy over a very short period of time, and an arc arises between the electrodes of the spark gap device which vaporizes water surrounding the path of the spark, thereby establishing a plasma-like state. The result is an explosion-like vaporization of the water, which produces an electro-hydraulic shock wave that spreads out in a circular fashion. A metallic, ellipsoid-shaped structure surrounds a rear portion of the spark gap, opposite the patient, to produce a focal point of the shock wave that coincides with a location in the pathological bone site at which the shock wave is to be focused. The size and shape of the ellipsoid dictate the position of the focal point. This device also requires that the patient be submerged in the water.

U.S. Pat. No. 4,979,501 to Valchanov et al., issued on Dec. 25, 1990, teaches a method and apparatus for treating pathologies with shock or "impact" waves for correction of delayed bone consolidation and bone deformations. The method comprises the steps of anesthetizing the patient, fixing the limb affected with the pathological bone condition, centering the pathological site of the bone on the shock wave focal point, treating the affected bone site once or consecutively, with 300 to 6000 impacts. The impacts have a frequency of 0.4–4.0 per second with a pulse duration of 0.5 to 4.0 microseconds for a period of 10–120 minutes. After these steps have been performed, the limb is immobilized for a period from 15 to 90 days.

The impact wave-generating device disclosed by Valchanov et al. generally consists of a vessel that contains a transmitting medium or acoustic liquid such as water. At a bottom portion of the vessel, opposed electrodes are disposed, which are adapted to produce a shock across the gap. Therefore, the patient is not submerged for treatment.

U.S. Pat. No. 4,896,673 to Rose et al., teaches a method and apparatus that utilize focused shock wave treatment of kidney stones in combination with localization using ultrasound or x-ray imaging. Rose et al. discloses that if the number and magnitude of the shock wave pulses are sufficient, the shock wave treatment may disintegrate a kidney stone.

Shock waves have also been used to treat soft tissue. For example, U.S. Pat. No. 5,316,000 to Chapelon et al. discloses an array of composite piezoelectric transducers for making an acoustic or ultrasonic therapy device for use in the treatment of varicose veins. U.S. Pat. No. 5,458,130 to Kaufman et al. discloses using shock waves to treat soft tissue such as cartilage, ligament, and tendons.

To date, shock waves have not been used in the medical field of orthodontics. Standard orthodontics for the treatment of malocclusion may typically require 18–30 months to complete, depending on the severity of the problem. Generally, orthodontic patients are anxious to finish their treatment in as short a period of time as possible. In an effort to speed up orthodontic treatment, surgical techniques have been expanded over recent decades. The most recent and most refined of these techniques has been presented by William and Thomas Wilcko, as Accelerated Osteogenic Orthodontics (AOO), and involves peeling back the gingival tissue from the cortical bone surrounding the teeth and then performing corticotomy. Corticotomy is a procedure that barely cuts through the cortical bone between the teeth with a rotary instrument. After the cuts have been made, certain bone augmentation procedures are performed to speed up the orthodontic treatment. The gingival flap is then replaced.

AOO causes a tissue metabolic process to be initiated, which is referred to as regional accelerated phenomenon (RAP). RAP creates an increase in bone remodeling that starts as a drastic demineralization of both medullary and cortical alveolar bone. Because the medullary bone has a much higher surface-to-volume ratio, and because the teeth are surrounded primarily by medullary bone, RAP renders the bone around the teeth largely into demineralized osteoid, a condition known as osteopenia. When osteopenia has thusly been established around teeth, it has been shown that orthodontic appliances can be used that enable treatment to be completed in about ⅓ of the amount of time typically required to treat malocclusion. One of the drawbacks to AOO is that it requires an invasive surgical procedure to initiate RAP and ostoepenia, which involves peeling back the gingival tissue and cutting through the cortical bone.

It would be desirable to provide a way to accelerate orthodontic treatment to enable treatment of malocclusion to be established without having to subject the patient to invasive surgery, such as that associated with AOO, for example.

SUMMARY OF THE INVENTION

The present invention provides methods for use in orthodontics for accelerating the treatment of malocclusion by noninvasively altering a condition of bone in a patient's jaw so that teeth held in generally fixed positions in the bone are able to be relatively easily and rapidly repositioned using orthodontic appliances. The alteration may be fracturing the medullary and/or cortical bone around the teeth and/or altering vascular, nerve and/or cellular characterisitics of the medullar and/or cortical bone. Once this has been accomplished, typical appliances may be used for treatment of malocclusion. Because the medullary and/or cortical bone has been fractured, and/or vascular, nerve and/or cellular characterisitics of the medullary and/or cortical bone have been altered, the appliances used to move the teeth to correct for malocclusion are capable of moving the teeth more rapidly, thereby enabling the process of treating malocclusion to be significantly accelerated in comparison to typical processes used for treatment of malocclusion. I In accordance with one embodiment, shock waves are used to alter the condition of bone in the patient's jaw. In accordance with another embodiment, tuned and sustained ultrasound waves and/or high intensity focused ultrasound (HIFU) waves are used to alter the condition of bone in the patient's jaw.

These and other features and advantages of the present invention will become apparent from the following description, drawings and claims.

DESCRIPTION OF THE PREFERRED EMBODIMENTS OF THE INVENTION

The present invention is directed to shortening the length of time required to treat malocclusion by using noninvasive stimuli that fractures the medullary and/or cortical bone around the teeth and/or alters vascular, nerve and/or cellular characterisitics of the medullar and/or cortical bone. Altering the condition of the bone in one or more of these ways enables the teeth to be moved much more rapidly using typical orthodontic appliances. The stimuli may be in the form of shock waves and/or ultrasound waves. In accordance with the present invention, it has been determined that extracorporeal shock waves generated in various ways, such as, for example, using electrohydraulic, electromagnetic, or piezoelectric devices, to fracture the medullary and/or cortical bone surrounding the teeth. Similarly, it has been determined that sustained resonating sound waves or high intensity focused ultrasound waves (HIFU), such as those delivered by medical ultrasound devices, can be used to set up standing waves or shock waves in medullary bone to thereby fracture the bone, either on a molecular or non-molecular level. Shock waves and ultrasonic waves also have a physiologic effect on bone tissue via vascular, nerve, or bone cell effects to induce osteopenia.

The cortical bone is generally a 1 to 3 millimeters (mm) thick bone structure that surrounds the medullary bone. The medullary bone is a sponge-like bone structure that surrounds the teeth and that is surrounded by cortical bone. The medullary bone is permeated with vascular and soft tissue, and is susceptible to a variety of tissue disruptions, including, for example, microbleeding, microhematoma, microscopic molecular and non-molecular bone fracturing, gross bone fracturing and mineral depletion in the very thin walls of the spongy medullary bone. These disruptions create cell-mediated changes that lead to the desired physiological effects that facilitate rapid tooth movement, as described below in more detail.

Figure 1:
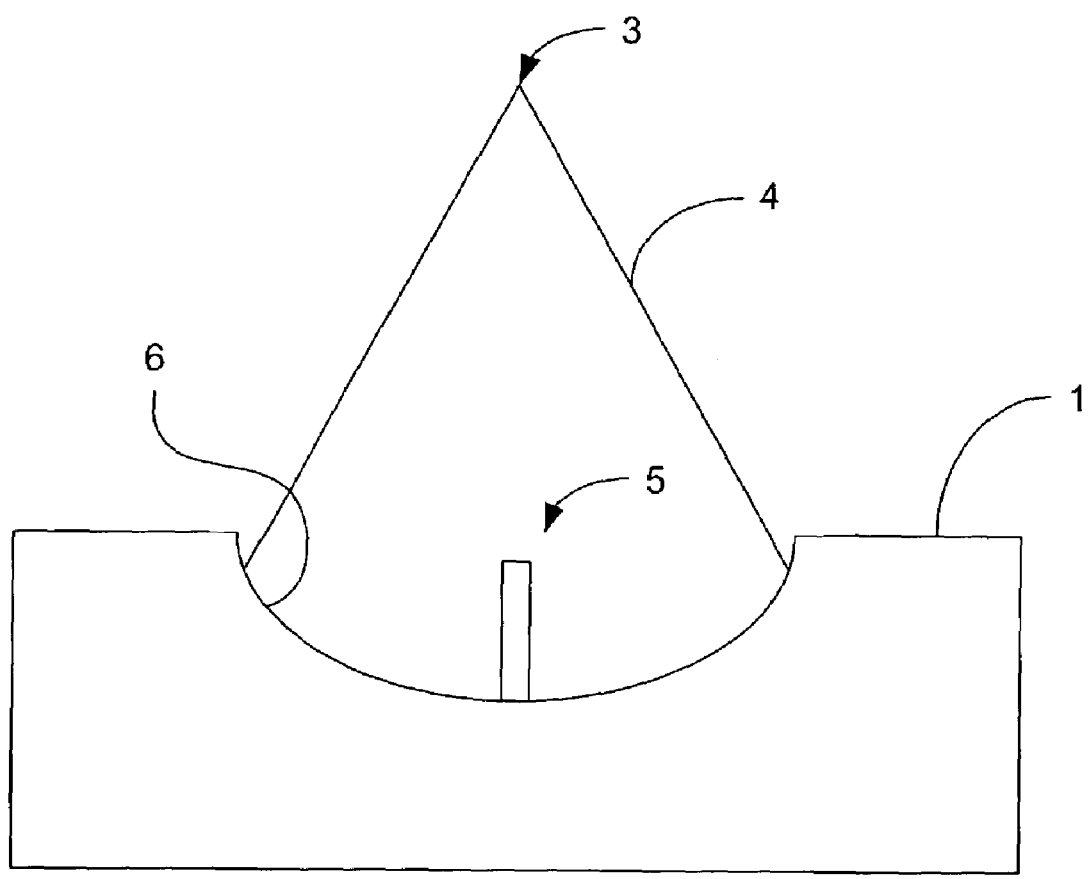
FIG. 1 is a top view of an example of a shock wave generating device that is suitable for use in performing the method of the present invention.

FIG. 1 is a top view of an example of a shock wave generating device that is suitable for delivering stimuli in the form of acoustical, shock waves, to a patient's gingival tissue in order to fracture the medullary and/or cortical bone. The device 1 comprises a shock wave reflector 2 that focuses shock waves generated by the device 1 at a focal point 3. The location of the focal point 3 is dictated by the geometry and dimensions of the reflector 2. The shock waves 4 propagate through water surrounding an electrode 5 when a bias voltage or current is applied to the electrode 5. The shock waves 4 are reflected by the surface 6 of the reflector 2 and converge at the focal point 3. The device 1 will be positioned at a location such that the focal point 3 will be in contact with the location on the gingival tissue that is to receive the stimuli.

Those skilled in the art will understand, in view of the description provided herein, how a suitable shock wave or ultrasound device can be selected or developed to appropriately apply shock waves and/or ultrasound waves. Devices are available in the market that are suitable for these purposes.

Figure 2:
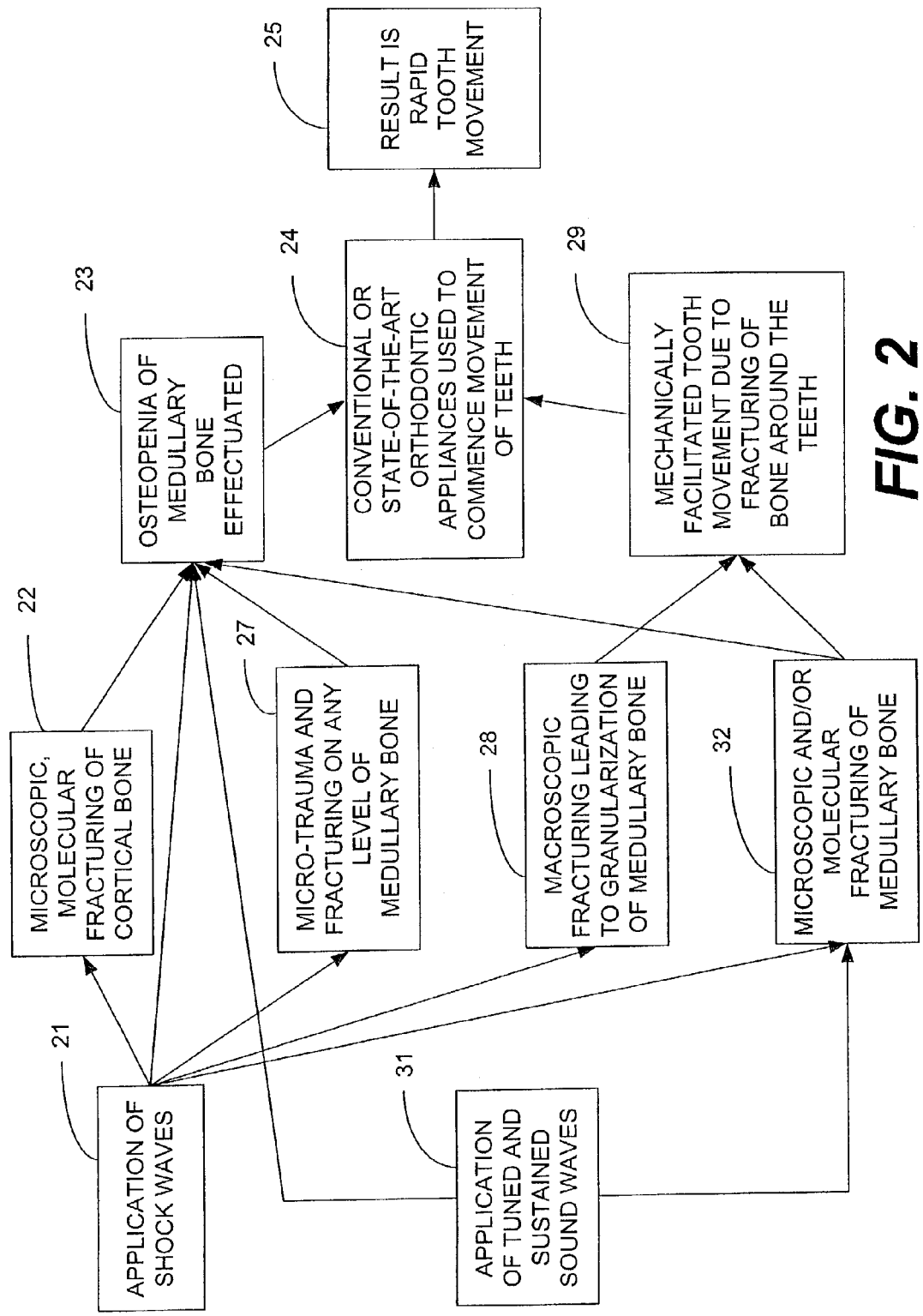
FIG. 2 is a flow chart illustrating the manner in which the method of the present invention in accordance with the preferred embodiment can be performed using shock waves and sound waves.

FIG. 2 is a flow chart illustrating the method of the present invention in accordance with the preferred embodiment for fracturing the medullary and/or cortical bone on either a microscopic crystalline (i.e., molecular) level, on a microscopic non-molecular level, and/or on a macroscopic level. As shown in FIG. 2, this fracturing of the bone about the teeth can be induced by applying shock waves, as indicated by block 21, and/or by applying tuned and sustained sound waves or high intensity focused ultrasound (HIFU) waves, as indicated by block 31. Depending on which of these bone-fracturing techniques and/or soft tissue disrupting techniques is used, different types, or levels, of fracturing and/or physiologic changes will occur. The procedure of the present invention that utilizes shock waves will be first be described, and then the procedure of the present invention that utilizes sustained sound waves and/or HIFU waves will be described.

With reference again to FIG. 2, the application of shock waves to gingival tissue at an appropriate location will result in fracturing of the medullary and/or cortical bone on one or more different levels, as indicated by blocks 22, 27, 28 and 32. The energy of the shock waves and the number of shock waves applied are adjusted to achieve the desired effect. Block 22 corresponds to applying shock waves to the extent that microfracturing of the cortical bone on a molecular level (i.e., fracturing the crystalline structure of the bone) occurs. Block 27 corresponds to shock wave application that produces micro-trauma to the medullary bone and thereby effectuating fracturing of the medullary bone on a molecular and/or non-molecular level. Block 28 corresponds to shock wave application that effectuates macrofracturing leading to granularization of the medullary bone (i.e., fracturing into very small parts, but not on a crystalline, or molecular, level). Block 32 corresponds to shock wave application that effectuates microscopic non-molecular fracturing and/or microscopic molecular fracturing of the medullary bone.

As indicated by the arrows from blocks 22 and 27 to block 23, the fracturing associated with blocks 22 and 27 leads to the condition of osteopenia. Alternatively, application of the shock waves can create physiologic changes that lead directly to the initiation of osteopenia, as indicated by the arrow from block 21 to block 23. Once the condition of osteopenia has been initiated, conventional or state-of-the-art orthodontic appliances can be used to treat the condition of malocclusion, as indicated by block 24. The result is rapid tooth movement, i.e., accelerated treatment of malocclusion, as indicated by block 25. As indicated by the arrows from blocks 28 and 32 to block 29, the application of shock waves can also lead to some degree of fracturing of the cortical and/or medullary bone that makes mechanically-facilitated tooth movement possible due to the fracturing of the bone around the teeth, as indicated by block 29. Once this condition has been established, conventional or state-of-the-art orthodontic appliances can be used to treat the condition of malocclusion, as indicated by block 24. The result is rapid tooth movement, i.e., accelerated treatment of malocclusion, as indicated by block 25. The arrow from block 32 to block 23 is meant to indicate that the fracturing represented by block 32 can also lead to the initiation of osteopenia, which enables orthodontic devices to be used to produce rapid tooth movement.

With reference to block 31, an ultrasound device is used to apply tuned and sustained sound waves and/or HIFU waves to the gingival tissue to cause a standing wave to be set up that is preferably at the resonant frequency associated with the crystalline, or molecular, structure of the medullary bone. The application of these sound waves results in microscopic non-molecular and/or microscopic molecular fracturing of the medullary bone, as indicated by block 32. This makes mechanically-facilitated tooth movement possible due to the fracturing of the bone around the teeth, as indicated by block 29. The arrow from block 32 to block 23 indicates that this microscopic fracturing may also lead to osteopenia. The arrow from block 31 to block 23 indicates that the use of an ultrasound device to apply tuned and sustained sound waves or HIFU waves to gingival tissue can cause physiologic changes in the vascular, nerve, and/or bone cells within the bone that effectuate osteopenia. In any event, application of tuned and sustained resonating sound waves and/or HIFU waves enables conventional or state-of-the-art orthodontic appliances to be used to treat the condition of malocclusion, as indicated by block 24. As is the case when using shock waves, the result is that rapid tooth movement is made possible, i.e., accelerated treatment of malocclusion, as indicated by block 25.

Figure 3:
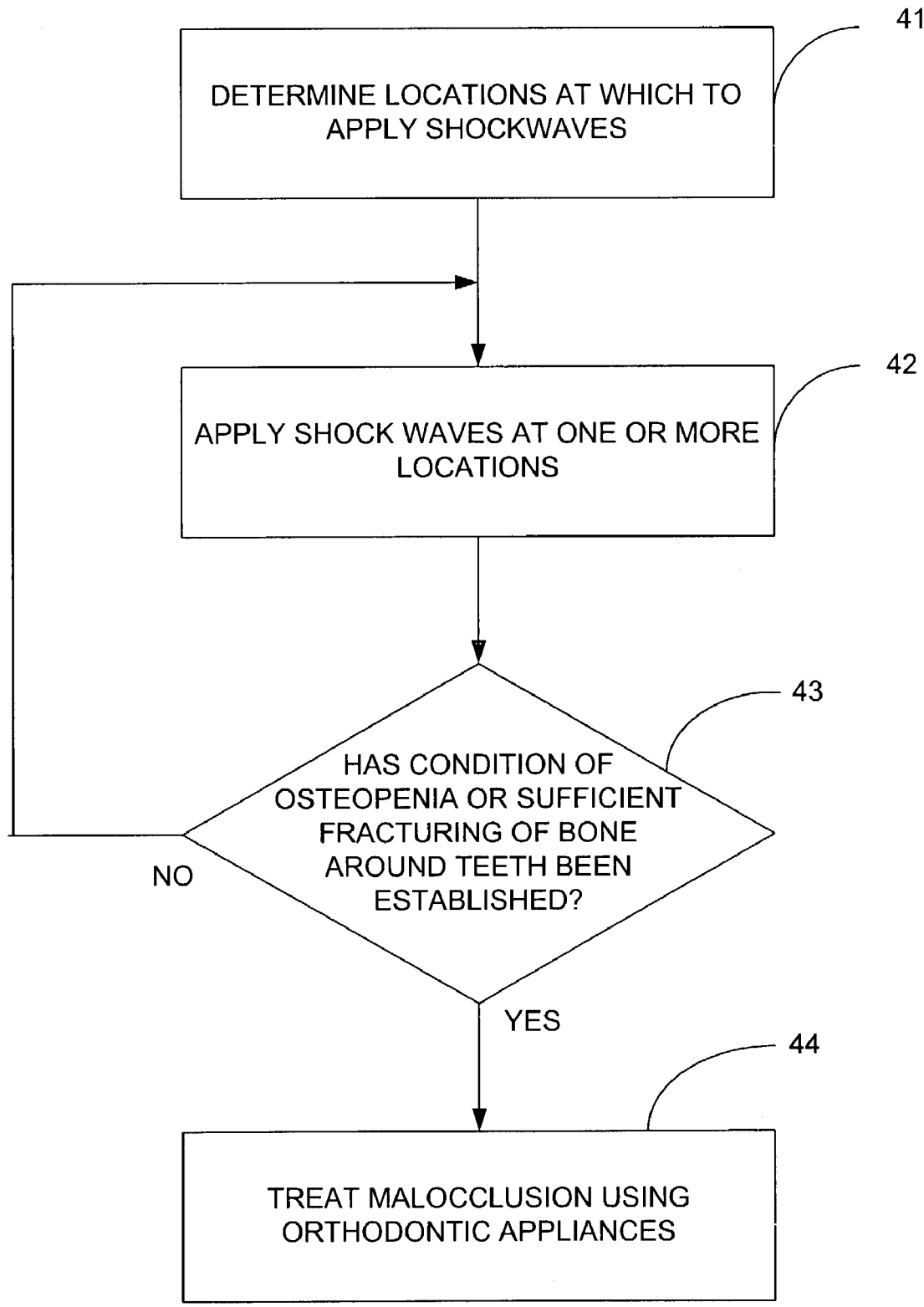
FIG. 3 is a flow chart further illustrating the method of the present invention in an embodiment in which shock waves are used in accordance with the embodiment shown in FIG. 2 to fracture the medullary and/or cortical bone and/or create conditions for osteopenia in the medullary bone.

FIG. 3 is a flow chart illustrating the method of the present invention for non-invasively accelerating tooth movement through application of shock waves. The healthcare worker determines locations at which shock waves are to be applied, as indicated by block 41. Shock waves are then applied at one or more locations, as indicated by block 42. A determination is then made as to whether the application of shock waves at the selected location(s) was sufficient to facilitate rapid tooth movement, as indicated by block 43. If not, more shock waves are applied at one or more locations, as indicated by the arrow from block 43 to block 42. If so, orthodontic appliances are used on the patient to treat malocclusion, as indicated by block 44.

Figure 4:
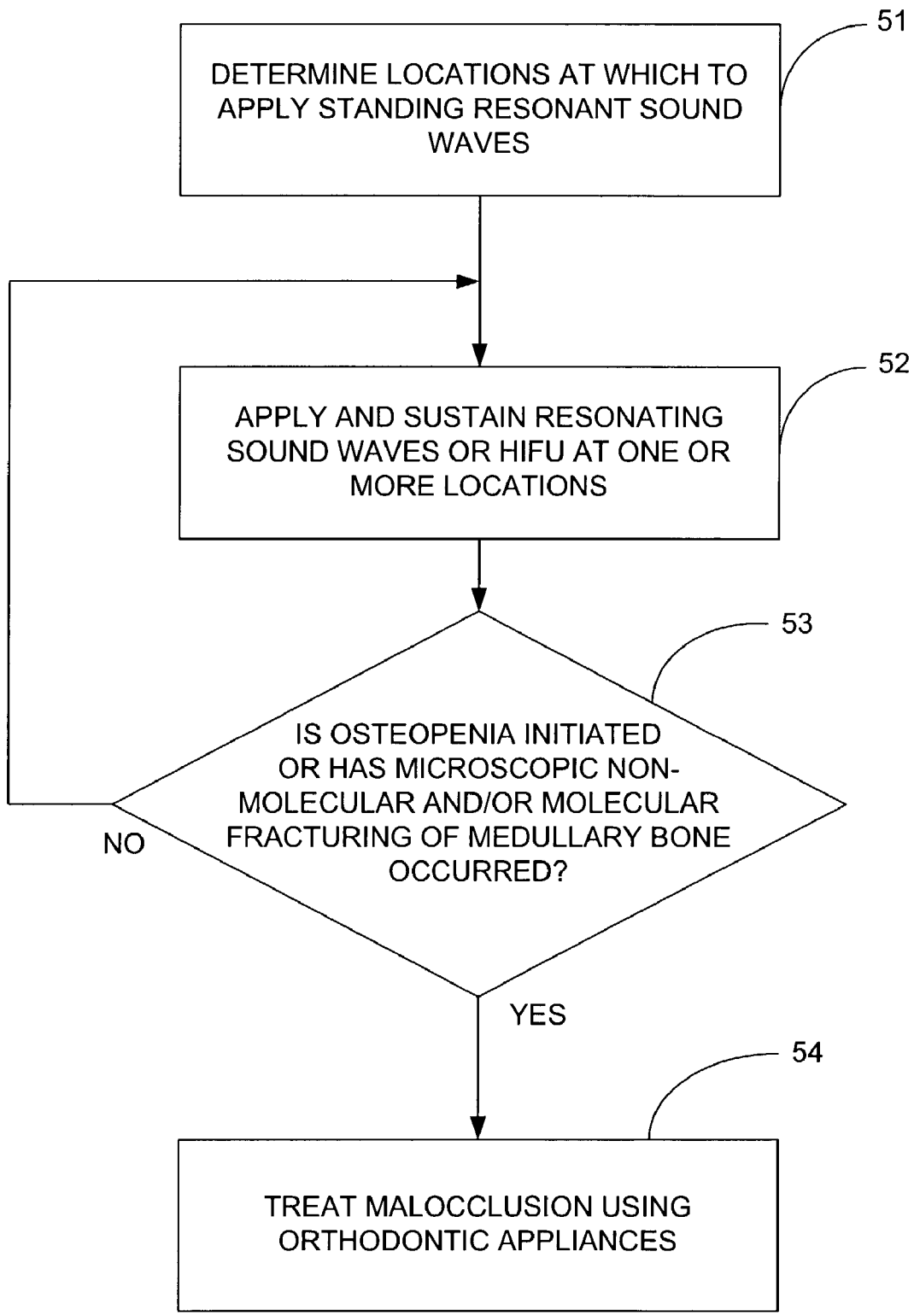
FIG. 4 is a flow chart further illustrating the method of the present invention in an embodiment in which ultrasound waves are used in accordance with the embodiment shown in FIG. 2 to fracture the medullary bone and/or create conditions for osteopenia in the the medullary bone.

FIG. 4 is a flow chart illustrating the method of the present invention for non-invasively accelerating tooth movement through application of sound waves. The healthcare worker determines one or more locations at which sound waves are to be applied, as indicated by block 51. Sound waves are then applied at one or more locations, as indicated by block 52. A determination is then made as to whether the application of sound waves at the selected location(s) was sufficient to facilitate rapid tooth movement, as indicated by block 53. If not, more sound waves are applied at one or more locations, as indicated by the arrow from block 53 to block 52. Step 52 may also entail adjusting the frequency and/or intensity of the sound waves to achieve the best result. If a determination is made at block 53 that the application of the sound waves at the selected location(s) was sufficient to facilitate rapid tooth movement, then orthodontic appliances are subsequently used on the patient to treat malocclusion, as indicated by block 54.

It should be noted that the present invention has been described with reference to preferred embodiments and that the invention is not limited to these embodiments. Those skilled in the art will understand how to perform the procedures discussed herein to produce appropriate fracturing of the cortical and/or medullary bone and/or initiate osteopenia, to accelerate the treatment for malocclusion. Also, techniques other than those discussed herein may be used to produce the necessary fracturing and/or condition of osteopenea, and the present invention includes the use of such other techniques.

What is claimed is:

1. A method for use in orthodontics for accelerating treatment of malocclusion, the method comprising the step of:
   non-invasively fracturing bone in a patient's jaw by applying shock waves to the patient's jaw so that maloccluded teeth are destabilized by reducing structural integrity of surrounding bone to enable the teeth to be relatively easily and rapidly repositioned using orthodontic appliances.

2. The method of claim 1, wherein the shook waves fracture cortical bone on a microscopic, non-molecular level.

3. The method of claim 2, wherein the microscopic fracturing of the cortical bone mechanically facilitates relatively easy and rapid repositioning of the teeth using orthodontic appliances.

4. The method of claim 3, wherein the microscopic fracturing of the cortical bone causes at least a component of Regional Accelerated Phenomenon (RAP) in medullary bone in the patient's jaw to be initiated, and wherein the initiation of RAP in the medullary bone enables the teeth to be relatively easily and rapidly repositioned using orthodontic appliances.

5. The method of claim 1, wherein the shock waves fracture medullary bone, and wherein the fracturing of the meciuliary bone enables the teeth to be relatively easily and rapidly repositioned using orthodontic appliances.

6. The method of claim 5, wherein the medullary bone is fractured on a microscopic, non-molecular level, the microscopic fracturing of the medullary bone causing at least a component of Regional Accelerated Phenomenon (RAP) in medullary bone to be initiated, and wherein the initiation of RAP in the medullary bone enables the teeth to be relatively easily and rapidly repositioned using orthodontic appliances.

7. The method of claim 5, wherein the medullary bone is fractured on a microscopic, molecular level, the microscopic fracturing of the medullary bone causing at least a component of Regional Accelerated Phenomenon (RAP) in medullary bone to be initiated, and wherein the initiation of RAP in the medullary bone enables the teeth to be relatively easily and rapidly repositioned using orthodontic appliances.

8. The method of claim 5, wherein the medullary bone is fractured on a macroscopic, non-molecular level, the macroscopic fracturing of the medullary bone mechanically facilitating relatively easy and rapid repositioning of the teeth using orthodontic appliances.

9. The method of claim 5, wherein the medullary bone is fractured on a microscopic, molecular level, the microscopic fracturing of the medullary bone mechanically facilitating relatively easy and rapid repositioning of the teeth using orthodontic appliances.

10. The method of claim 1, wherein the shock waves are tuned to approximately a resonant frequency of the bone.

* * * * *